United States Patent
Gurjar et al.

(10) Patent No.: US 9,447,094 B2
(45) Date of Patent: Sep. 20, 2016

(54) PYRIDONE DERIVATIVES AS ACID SECRETION INHIBITORS AND PROCESS FOR PREPARATION THEREOF

(71) Applicant: Emcure Pharmaceuticals Limited, Bhosari, Pune (IN)

(72) Inventors: Mukund Keshav Gurjar, Pune (IN); Narendra Kumar Tripathy, Pune (IN); Golakchandra Sudarshan Maikap, Pune (IN); Rajendra Dagesing Mahale, Pune (IN); Tushar Pandurang Khaladkar, Pune (IN); Ashok Tukaram Chaudhari, Pune (IN); Sanjay Shankar Pawar, Pune (IN); Vijay Keshav Kalhapure, Pune (IN); Samit Satish Mehta, Pune (IN)

(73) Assignee: Emcure Pharmaceuticals Limited (IN)

( * ) Notice: Subject to any disclaimer, the term of this patent is extended or adjusted under 35 U.S.C. 154(b) by 0 days.

(21) Appl. No.: 14/703,515

(22) Filed: May 4, 2015

(65) Prior Publication Data

US 2015/0232467 A1    Aug. 20, 2015

Related U.S. Application Data

(63) Continuation-in-part of application No. PCT/IN2013/000699, filed on Nov. 18, 2013.

(30) Foreign Application Priority Data

Nov. 26, 2012    (IN) .................. 3360/MUM/2012

(51) Int. Cl.
  *C07D 401/14*    (2006.01)
  *C07D 471/04*    (2006.01)
  *C07D 401/04*    (2006.01)

(52) U.S. Cl.
  CPC ........... *C07D 471/04* (2013.01); *C07D 401/04* (2013.01); *C07D 401/14* (2013.01)

(58) Field of Classification Search
  CPC .................................................. C07D 401/14
  USPC ..................................................... 546/273.4
  See application file for complete search history.

(56) References Cited

U.S. PATENT DOCUMENTS

| | | | |
|---|---|---|---|
| 4,636,499 A | 1/1987 | Brandstrom et al. | |
| 4,769,456 A | 9/1988 | Nohara et al. | |
| 5,162,317 A | 11/1992 | Souda et al. | |

FOREIGN PATENT DOCUMENTS

| | | |
|---|---|---|
| CN | 101486706 | 7/2009 |

OTHER PUBLICATIONS

Kandulski et al. I, "Helicobacter pylori, etc.," Digestive and Liver Disease 40 (2008) 619-626.*
Lochhead et al., "Helicobacter pylori, etc.," Best Practice & Research Clinical Gastroenterology, 21 (2), pp. 281-297, 2007.*
Cecil Textbook of Medicine, Bennett et al. ed W.B. Saunders Co., Philadelphie, 1997, 20th ed, vol. 1, 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Golub et al, Science, vol. 286, Oct. 15, 1999, pp. 531-537.*
Lamers, "Is there s Need, etc.," Digestion 1989; 44 (suppl 1):4-8.*
Zollinger-Ellison syndrome-Mayo Clinic.com-print May 16, 2012.*
Weber et al., "Studies on the, etc.," Gastroenterology 1997;112: 84-91.*
Monkemuller et al., "Drug treatment, etc.," World J Gastroenterol 2006: 12(17) 2694-2700.*
Talley et al., II "Efficacy of omeprazole, etc.," Aliment Pharmacol Ther 1998; 12: 1055-1065.*
Talley et al. I, "Whither dyspepsia?, etc.," J of Gastroenterology and Hepatology 24 (2009) Suppl. 3: S20-S28.*
Kuipers, "Helicobacter pylori, etc.," Aliment Pharmacol Ther 1997: 11 (Suppl. 1), 71-88.*
Schubert, "Gastric Secretion", Current Opinion in Gastroenterology 2007, 23:595-601.*
Sherman et al., "Role of Sonic, etc.," World J Gastrointest Pathophysiol Dec. 15, 2011; 2(6): 103-108.*
Kuipers et al., "Review Article, etc.," Aliment Pharmacol Ther 1995, 9: 331-340.*
Kandulski et al. II, "Helicobacter pylori, etc.," Curr Opin Gastroenterol 2014, 30:402-407.*
Freston, "Review Article, etc.," Aliment Pharmacol Ther 2001:15 (Suppl 2), 2-5.*
Venerito et al., "Interaction of, etc.," Helicobacter 15: 239-250 (2010).*
Brandstrom, Arne, et al., Chemical Reactions of Omeprazole and Omeprazole Analogues. I. A Survey of the Chemical Transformations of Omeprazole and its Analogues, Acta Chemica Scandinavica, vol. 143, Dec. 1989, pp. 536-548.
Sturm, Ernst, et al., H+ K+ ATPase Inhibiting 2-[(2-pyridylmethyl)sulfinyl]benzimidazoles as Mimics for the Inhibited Enzyme, J. Organic Chemistry, No. 20, vol. 52, Oct. 1987, pp. 4573-4581.
Gupta, Hanuman, et al., Study of Acid Catalyzed Reactions of Proton Pump Inhibitors at D.M.E., Portugaliae Electrochimica Acta, 26/5, Apr. 2008, pp. 433-448.

(Continued)

*Primary Examiner* — Patricia L Morris
(74) *Attorney, Agent, or Firm* — Florek & Endres PLLC

(57) ABSTRACT

The present invention relates to the preparation of stable pyridone disulphide derivatives having general formula (I) and its stereoisomers, which are useful in the treatment of gastrointestinal disorders. Pyridone disulphide derivatives (I) wherein, $R_1$, $R_2$ and $R_3$ are independently alkyl, alkoxy, halogen, halogenated alkoxy, halogenated alkyl, hydrogen and could be the same or different and X is CH or N. $R_1$ is methyl, methoxy, fluorine, trifluoromethyl, difluoromethoxy and hydrogen, $R_2$ is methyl, methoxy and hydrogen, and $R_3$ is methyl and hydrogen.

16 Claims, No Drawings

(56) References Cited

OTHER PUBLICATIONS

Tutunji, Maha, et al., An In Vitro Investigation on Acid Catalyzed Reactions of Proton Pump Inhibitors in the Absence of an Electrophile, International Journal of Pharmaceutics, vol. 323, May 2006, pp. 110-116.

Yang, Jie, International Search Report in PCT/IN2013/000699, 5 pages, Apr. 2014, State Intellectual Property Office of the P.R. China, Beijing, China.

Dantzig, H., et al., Studies of the Mechanism of Action of A80915A, A Semi-Naphtolquinone Natural Product, As an Inhibitor of Gastric (H+/K+)-ATPase, Biochem. Pharmacol., 1991, 42:2019.

Scott, C.K. et al, Inhibition of H+K+ATPase Activity by SCH 28080 and SCH 32651, Eur. J Pharmacol, Jun. 1985, vol. 112(2), pp. 268-270.

Keeling D.J., et al., Studies on the Mechanism of Action of Omeprazole, Biochem. Pharmacol., vol. 34(16), Aug. 1985, pp. 2967-2973.

Bhattacharya, S., et al., Healing Property of the Piper Betelphenol, Allylpyrocatechol Against Indomethacin-Induced Stomach Ulceration and Mechanism of Action, World J Gastroenterol, vol. 13(27), 2007, pp. 3705-3713.

Lee, A., Animal Models of Gastroduodenal Ulcer Disease, Bailliere's Best Pract. Res. Clinic Gastroenterol, vol. 14(1), 2000, pp. 75-96.

\* cited by examiner

PYRIDONE DERIVATIVES AS ACID SECRETION INHIBITORS AND PROCESS FOR PREPARATION THEREOF

This application is a continuation-in-part of International Application No. PCT/IN2013/000699, filed Nov. 18, 2013, which in turn claims priority to Indian Patent Application No. 3360/MUM/2012, filed Nov. 26, 2012.

FIELD OF THE INVENTION

The present invention relates to stable pyridone disulphide derivatives of general formula (I), their preparation and utilization for the treatment of ailments related to the stomach and intestine.

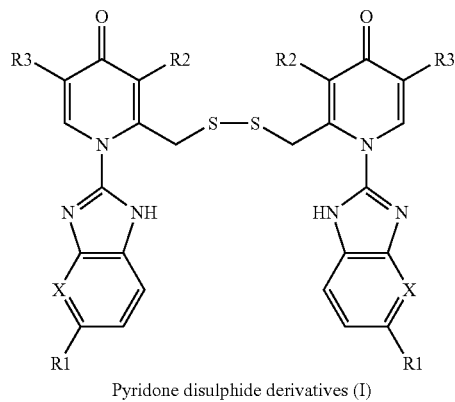

Pyridone disulphide derivatives (I)

Wherein, $R_1$, $R_2$ and $R_3$ are alkyl, alkoxy, halogen, halogenated alkoxy, halogenated alkyl, hydrogen and could be same or different and X is CH or N.

$R_1$ is methyl, methoxy, fluorine, trifluoromethyl, difluoromethoxy and hydrogen, $R_2$ is methyl, methoxy and hydrogen, $R_3$ is methyl and hydrogen.

BACKGROUND OF THE INVENTION

Gastrointestinal disorders such as peptic ulcers, gastroesophageal reflux and heartburns arising out of excessive secretion of acidic gastric fluids are amongst the widely encountered diseases in modern age. These diseases, if not controlled, have a tendency to aggravate and ultimately result in gastric cancer. The initial treatment for this indication involved use of histamine-$H_2$-receptor antagonists such as cimetidine as acid secretion inhibitors, which was later followed by introduction of the proton-pump inhibitors (PPIs), collectively known as the prazoles.

The vast majority of the proton-pump inhibitors belonging to prazole group of compounds are benzimidazole derivatives comprising of two heterocyclic moieties, imidazole and pyridine which are linked through a methylene sulfinyl [—$CH_2S(O)$—] group. The mode of action involves inhibition of gastric acid secretion in the lumen of the stomach by blockage of ($H^+/K^+$)ATPase enzyme of the parietal cell, which is responsible for gastric acid production and is located in the secretory membranes of the parietal cells. Incidentally, the prazole group of compounds are by themselves, not active inhibitors of this enzyme but are transformed within the acid compartments of the parietal cells into the active inhibitors.

Portugaliae Electrochimica Acta (2008), 433-448 discloses that in case of omeprazole, the inactive drug is converted to its active form by a probable mechanism which involves protonation and removal of a water molecule to form a sulfenamide intermediate of formula (P1). This intermediate reversibly reacts with the sulfenic acid from which it has been generated and leads to the molecule (P2), which possesses a disulfide linkage between the benzimidazo pyridine fragments. (Scheme-1)

Scheme-1: Mechanism for formation of sulfenamide intermediate and disulfide derivative

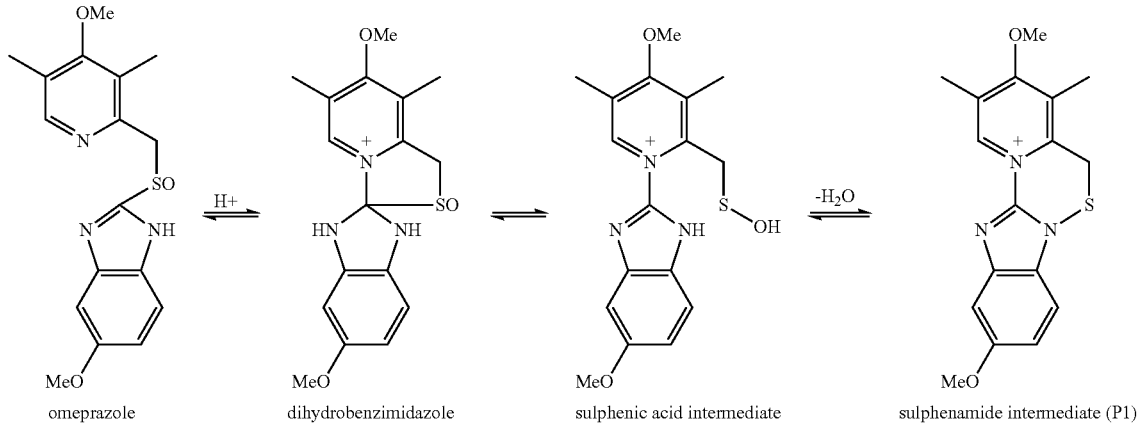

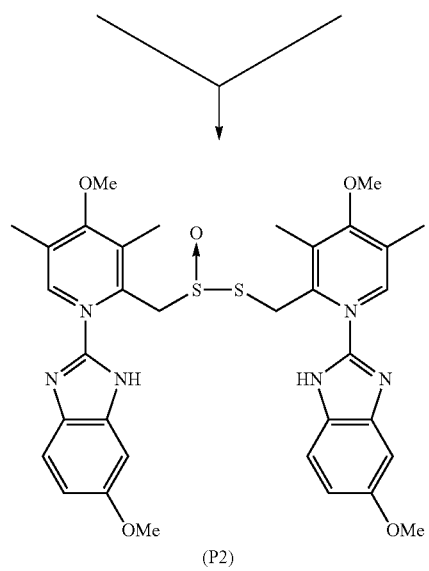

(P2)

The intermediate (P1), as discussed in Acta Chemica Scandinavica (1989), 43, 536-548, also undergoes aryl oxygen cleavage on treatment with hydrochloric acid to provide a pyridone derivative (P3) (Scheme-2).

Scheme-2: Reaction of sulfenamide (P1) to pyridone derivative (P3)

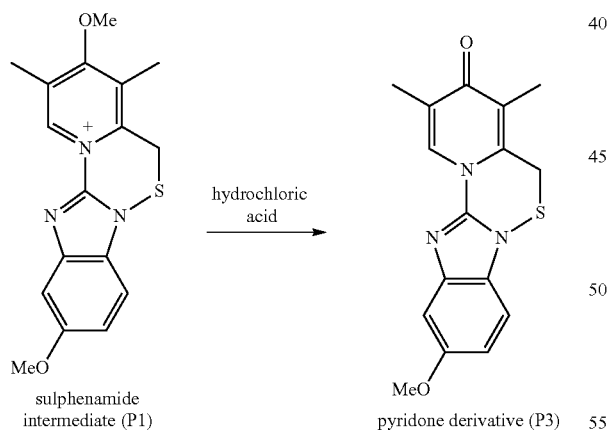

sulphenamide intermediate (P1) → pyridone derivative (P3)

The pyridone derivative (P3) gets further converted to compound (P4), similar to the disulfide compound (P2). Herein, it is pertinent to note that the pyridone derivative (P3) is known to be an unstable intermediate in the reactions of prazoles occurring in the acidic environment and readily converts to the disulfoxide derivative (P4).

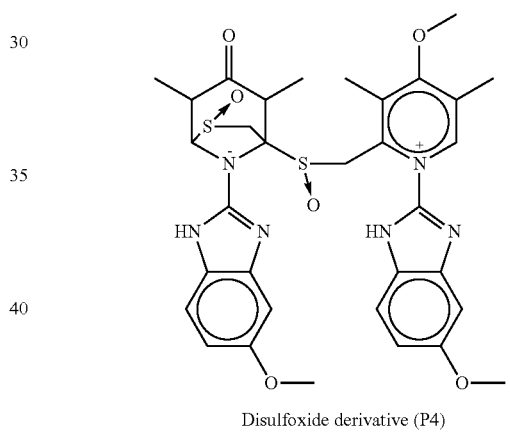

Disulfoxide derivative (P4)

It has also been reported that sulfenamides characterized by structures similar to compound (P1) are difficult to isolate and are usually isolated as acid addition salts.

U.S. Pat. No. 4,636,499 discloses methods for the preparation of the sulfenamides which can be employed for providing gastrointestinal cytoprotective effects during the treatment of gastrointestinal inflammatory diseases in mammals. The process comprises treatment of the respective prazole having a sulfoxide functional group with prohibitively expensive acids like $HPF_6$, $HBF_4$ or $HAuCl_4$. Hence, the resulting sulfenamide is in the form of an acid addition salt with the said acids, which unfortunately cannot be administered as such and needs to be converted to its free base followed by optional treatment with pharmaceutically acceptable acids.

U.S. Pat. No. 4,769,456, U.S. Pat. No. 5,162,317 also discloses methods for preparing sulphenamides, which apparently due to difficulty in isolation of the product are isolated as their salts with costly acids like fluoroboric acid, tetrafluoroboric acid or hexafluorophosphoric acid and not suitable for therapeutic use.

The present inventors, while carrying out research for identifying compounds that are themselves active inhibitors of gastric acid secretion in the stomach, through serendipity were successful in isolating compounds of formula (I) in a stable form. These compounds were found to exhibit instant therapeutic action against gastrointestinal disorders, without being converted further into any other active form.

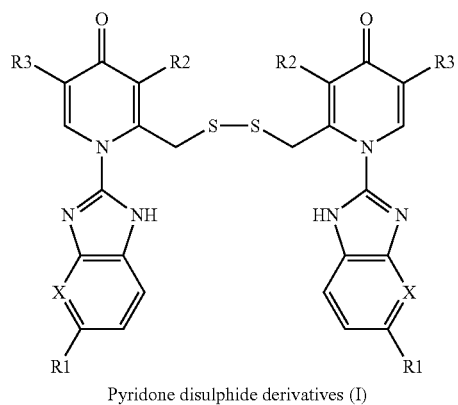

Pyridone disulphide derivatives (I)

wherein, $R_1$, $R_2$ and $R_3$ are independently alkyl, alkoxy, halogen, halogenated alkoxy, halogenated alkyl, hydrogen and could be the same or different and X is CH or N, $R_1$ is methyl, methoxy, fluorine, trifluoromethyl, difluoromethoxy and hydrogen, $R_2$ is methyl, methoxy and hydrogen, $R_3$ is methyl and hydrogen.

After an extensive study of the literature reports relating to the active compounds for gastrointestinal secretion inhibitory activity of prazoles, it was found that compounds of the invention having formula (I) were novel. Earlier, it was not possible to synthesize or isolate these compounds due to their unstable nature. Further, it was also found that the invented compounds having the pyridone moiety and the disulfide linkage were different from similar disulfide compounds (compound P2) disclosed in International Journal of Pharmaceutics (2006), 323, p. 110-116.

Another noteworthy finding about compounds of formula (I) was that they were found to be at least six times more potent than the prazole compounds, This would significantly lower the dosage of the active ingredient and also minimize any untoward side effects that are associated with higher dosage as compared to prior art compounds having similar therapeutic action.

The compounds of the embodied invention were prepared and isolated as stable, crystalline or amorphous solids, depending upon the structure of the compound and the method employed for their isolation.

OBJECT OF THE INVENTION

An object of present invention is to provide stable, crystalline or amorphous pyridone disulfide compounds of formula (I) and its stereoisomers useful as proton pump inhibitors for exhibiting gastric acid secretion inhibitory activity.

A further object of the invention is to obtain pyridone disulfide derivatives of formula (I) having desired purity and with associated impurities conforming to regulatory limits.

SUMMARY OF THE INVENTION

An aspect of the present invention is to provide stable pyridone disulfide compounds of formula (I).

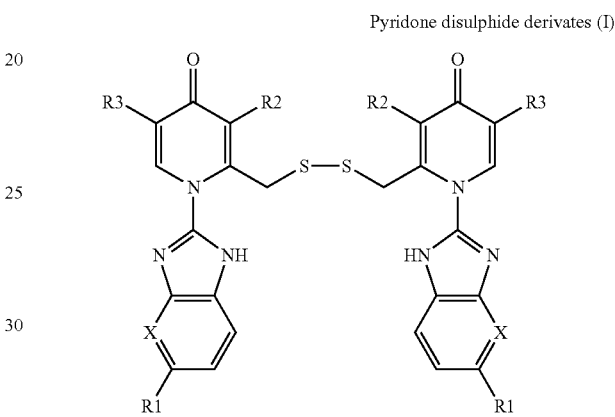

Pyridone disulphide derivates (I)

wherein, $R_1$, $R_2$ and $R_3$ are independently alkyl, alkoxy, halogen, halogenated alkoxy, halogenated alkyl, hydrogen and could either be the same or different and X is CH or N $R_1$ is methyl, methoxy, fluorine, trifluoromethyl, difluoromethoxy and hydrogen, $R_2$ is methyl, methoxy and hydrogen, $R_3$ is methyl and hydrogen.

Yet another aspect of the present invention is to provide a process for the preparation and isolation of stable pyridone disulfide derivatives of formula (I) comprising treatment of compound (IV) with a dealkylating agent to give compound of formula (V) followed by oxidation to give compound of formula (VI) and further treatment with an acid in presence of a solvent in the pH range of 4.5 to 8.5 to provide a compound of formula (I) conforming to regulatory specifications.

DETAILED DESCRIPTION OF THE INVENTION

In an embodiment, the present invention provides novel pyridone disulfide derivatives of formula (I), a process for their preparation and isolation of stable compounds of formula (I) in the pH range of 4.5 to 8.5. The invention also includes the preparation of stereoisomeric isomers of stable pyridone disulfide derivatives.

Scheme-3: Method embodied in the present invention for preparation of pyridine disulphide derivatives of formula (I)

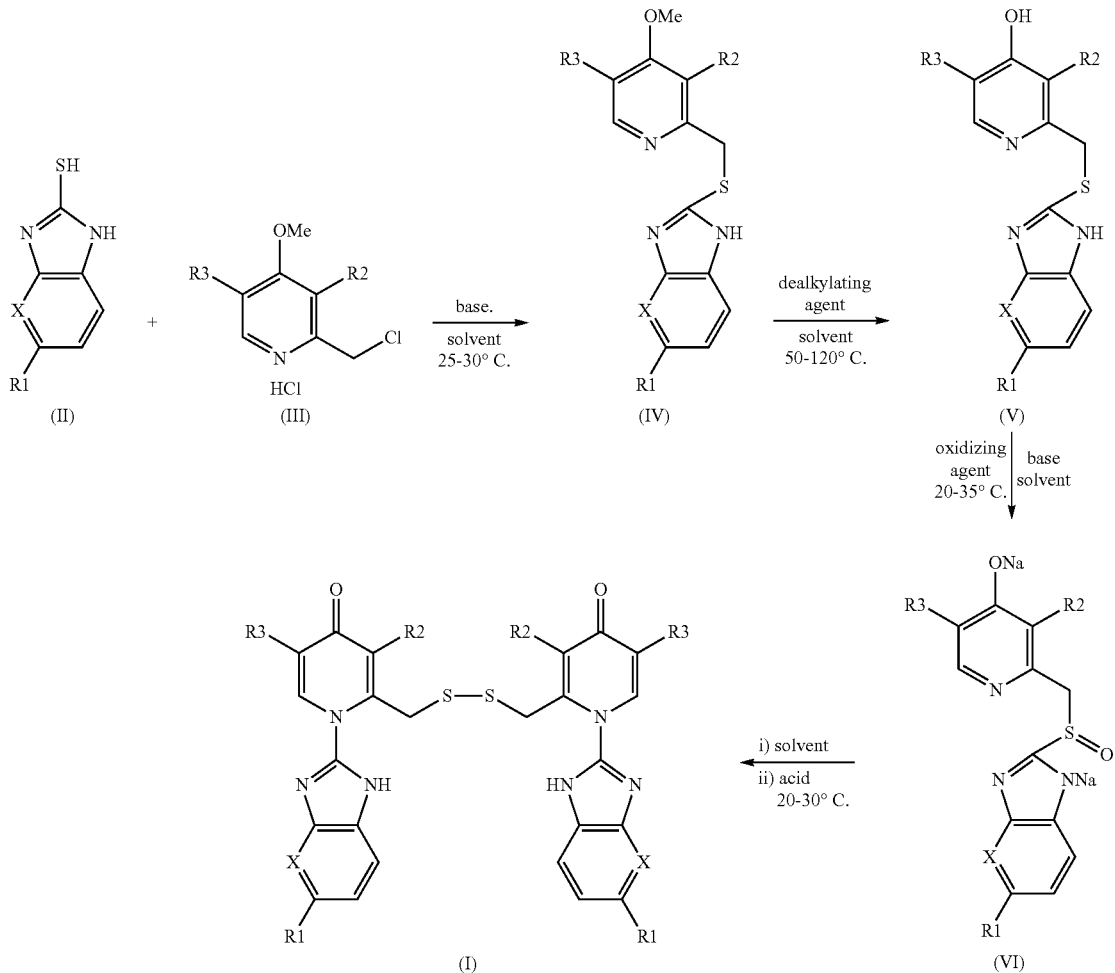

The meaning of term 'stable' used herein indicates that the compound of formula (I) is obtained in a stable form, crystalline or amorphous, not easily prone to degradation.

In yet another embodiment, the present invention provides a process for preparation and isolation of novel pyridone disulfide derivatives of formula (I), comprising of the following steps.

Step 1 involves reaction of substituted benzimidazo-2-thiol or substituted imidazo-pyridine-2-thiol (compound II) with substituted-2-chloromethyl-4-methoxy-pyridine derivative (compound III) in presence of a base and solvent to give substituted methoxy-2-pyridinyl-methylsulfidyl benzimidazole or the corresponding imidazo-pyridine derivative (compound IV).

The base was selected from the group comprising of sodium hydroxide, potassium hydroxide, calcium hydroxide, barium hydroxide etc. The solvent was selected from the group comprising of water, methanol, ethanol, isopropanol, butanol etc. and mixtures thereof.

The reaction was carried out at 20-40° C. After completion of the reaction as monitored by TLC, the mixture was filtered to give the respective substituted methoxy-2-pyridinyl-methylsulfidyl benzimidazole derivative or imidazo-pyridine derivative (compound IV) having desired purity.

Step 2 involved regioselective dealkylation of substituted methoxy-2-pyridinyl-methylsulfidyl benzimidazole or imidazo-pyridine derivative (compound IV) in presence of a dealkylating agent and a solvent to give compound of formula (V).

Various dealkylating agents such as sodium sulfide, hydrobromic acid, aluminium chloride etc. were used. In case of sodium sulfide, the reaction was carried out in the temperature range of 80 to 110° C., in presence of a solvent. The solvent was selected from the group comprising of nitriles, alcohols, polar aprotic solvents such as N-methyl pyrrolidone, dimethyl formamide, dimethyl acetamide water or mixtures thereof.

After completion of the reaction based on TLC, the reaction mass was cooled and neutralized with an acid such as acetic acid. Filtration of the obtained solid and drying gave the respective substituted hydroxy-2-pyridinyl-methylsulfidyl-benzimidazole or imidazo-pyridine derivative (compound V) having desired purity.

Alternatively, the dealkylation was also carried out by employing aqueous hydrobromic acid or using Lewis acid halides such as aluminium chloride, zinc chloride, optionally in presence of decanethiol. The reaction was carried out at a temperature ranging from 50-110° C., depending upon the type of the dealkylating reagent used.

After completion of the reaction as monitored by TLC, the product was isolated by concentrating the mixture and adding water followed by addition of an organic solvent like methanol to the aqueous layer at around neutral pH to obtain the desired product of formula (V).

Step 3 comprised treatment of substituted hydroxy-2-pyridinyl-methylsulfidyl-benzimidazole or imidazo-pyridine derivative (compound V) with an oxidizing agent to give compound of formula (VI).

This step involved treatment of compound of formula (V) with an oxidizing agent such as (10)-camphorsulfonyl oxaziridine (CSO) and its stereoisomers or an alkali metal hypochlorite to provide the sulfoxide derivative of formula (VI). The sulfide derivative (V) was treated with the oxidizing agent at 20-35° C. in presence of a base and organic solvent like isopropanol.

The base was selected from inorganic or organic bases. The inorganic base was selected from the group comprising of alkali metal hydroxides, carbonate and bicarbonates etc. while the organic base was selected from DBU, triethyl amine, diisopropyl ethyl amine etc.

The solvent was selected from the group comprising of alcohols such as methyl alcohol, ethyl alcohol, isopropyl alcohol etc. or mixtures thereof. After completion of reaction, as monitored by TLC, the reaction mass was filtered and the filtrate concentrated to get the desired compound (VI) which was optionally treated with organic solvents such as methanol, methyl tertiary butyl ether, toluene etc. or used as such for further reaction.

When oxidation was carried out using hypochlorite, compound (V) was added to a mixture of sodium hydroxide, water and methanol, followed by addition of sodium hypochlorite solution and the reaction was carried out at 20-35° C. The reaction was monitored by TLC and after completion, the reaction mass was extracted with an organic solvent and the organic layer was then concentrated to give the desired compound (VI).

Alternatively, after completion of oxidation reaction, the mass was carried forward for the next reaction. The pH of the reaction mass was adjusted in range of 4.5 to 8.5 using acid and the mass was stirred at 20-35° C. Optionally, an organic solvent such as methanol or ethyl acetate or solvent mixture was added during stirring and resulting solid was filtered after completion of the reaction as monitored by TLC, to give compound of formula (I).

Step 4 comprised treatment of compound (VI) with an acid in a solvent to obtain pH between 4.5 and 8.5, preferably 6.5 to 8, which was then stirred and filtered to obtain the desired compound (I).

The solvent was selected from the group comprising of water and organic solvents or mixtures thereof. The organic solvent was selected from the group comprising of ethers, esters, alcohols, ketones, hydrocarbons and halogenated hydrocarbons. The ethers were selected from the group comprising of dimethyl ether, dimethoxyethane, methyl-tertiary butyl ether etc. The solvents were selected from the group comprising of ethyl acetate, acetone, methanol, toluene, xylene, dichloromethane etc.

The acid employed was selected from an organic or mineral acid or a mixture thereof. The mineral acid was selected from the group comprising of hydrochloric acid, sulfuric acid and nitric acid. The organic acid was selected from the group comprising of acetic acid, citric acid, propionic acid, lactic acid etc., but preferably acetic acid.

In this step, the acid was slowly added with stirring to the mixture of compound (VI) and solvent(s) at 20-35° C., till the desired pH was obtained. The desired pH range varied for different substrates in the class of compound (VI) and ranged from 4.5 to 8.5 but preferably between 6.5 and 8.0.

After completion of the reaction, the desired compound of formula (I) separated out from the reaction mixture, filtered and dried. Optionally, the compound of formula (I) was subjected to purification procedures such as crystallization, solvent treatment, treatment with acid, column chromatography etc. to obtain the desired purity.

The desired compounds were obtained as stable, crystalline or amorphous solids and were characterized by $^1$H NMR, $^{13}$C NMR and MS.

The different compounds obtained by varying the substituent in the general formula (I) are provided in Tables 1A and 1B.

TABLE 1A

Pyridone Bisulphide Derivatives of formula (I-A), X=CH

| Name of the Compound | Substituents | | |
|---|---|---|---|
| | $R_1$ | $R_2$ | $R_3$ |
| I-A-1 | H | H | H |
| I-A-2 | H | $CH_3$ | $CH_3$ |
| I-A-3 | H | $OCH3$ | H |
| I-A-4 | $CH_3$ | $CH_3$ | $CH_3$ |
| I-A-5 | $CH_3$ | $OCH_3$ | H |
| I-A-6 | $OCH_3$ | $CH_3$ | $CH_3$ |
| I-A-7 | $OCH3$ | $OCH_3$ | H |
| I-A-8 | F | $CH_3$ | $CH_3$ |
| I-A-9 | $CF_3$ | $OCH_3$ | H |
| I-A-10 | $OCHF_2$ | $CH_3$ | $CH_3$ |
| I-A-11 | $OCHF_2$ | $OCH_3$ | H |
| I-A-12 | H or $CH_3$ | $CH_3$ | $CH_3$ |
| I-A-13 | $CH_3$ or $OCHF_2$ | $CH_3$ | $CH_3$ |
| I-A-14 | H or $OCHF_2$ | $CH_3$ | $CH_3$ |

TABLE 1B

Pyridone Disulphide Derivatives of formula (I-B), X=N

| Name of the Compound | Substituents | | |
|---|---|---|---|
| | $R_1$ | $R_2$ | $R_3$ |
| I-B-1 | H | $CH_3$ | $CH_3$ |
| I-B-2 | $OCH_3$ | $OCH_3$ | H |
| I-B-3 | $OCH_3$ | $CH_3$ | $CH_3$ |

For clinical use, the compounds of the invention were utilized for pharmaceutical formulations for oral, rectal, parenteral or other modes of administration. The pharmaceutical formulation contains a compound of the invention in combination with a pharmaceutically acceptable carrier. The carrier may be in the form of a solid, semisolid or liquid diluent, or a capsule. Usually the amount of active compound is between 0.1 and 95.0% by weight of the preparation.

When the compound of the present invention is to be administered as a therapeutic or preventive agent for peptic ulcer, it may be orally administered as powder, granule, capsule or syrup. Alternately, it may be parenterally administered in the form of suppositories, injections, external preparations or intravenous drips. The dose may vary depending on the condition, age and ulcer type of the patient. It may be administered in a dose of approximately 0.01 to 200 mg/kg/day, preferably 0.05 to 50 mg/kg/day and still preferably 0.1 to 10 mg/kg/day in one to several portions.

It may be formulated in a conventional manner by using conventional pharmacological carriers. When a solid preparation for oral administration is to be produced, for example, the active component is mixed with filler as well as a binder, a disintegrating agent, a lubricant, a colorant and/or a corrigent, if required. The obtained mixture is then formulated into tablets, coated tablets, granules, powders or capsules in a conventional manner.

Examples of fillers include lactose, corn starch, white sugar, glucose, sorbitol, crystalline cellulose and silicon dioxide. Examples of binder include polyvinyl alcohol, polyvinyl ether, methylcellulose, gum arabic, tragacanth, gelatin, shellac, hydroxypropyl-cellulose, hydroxypropyl starch and polyvinylpyrrolidone. Example of disintegrating agent includes starch, agar, gelatin powder, crystalline cellulose, calcium carbonate, sodium hydrogen carbonate, calcium citrate, dextrin and pectin. Examples of the lubricant include magnesium stearate, talc, polyethylene glycol, silica and hardened vegetable oils. As the colorant, pharmacologically acceptable ones may be employed. Examples of the corrigent include cocoa powder, mentha herb, aromatic powder, mentha oil, borneol and cinnamon powder. Needless to say, these tablets or granules may be coated with, for example, sugar or gelatin.

When an injection is to be produced, the active component is mixed with various additives such as a pH modifier, a buffer, a stabilizer or a solubilizing agent, if required. Thus a subcutaneous, intramuscular or intravenous injection is obtained.

The principles, preferred embodiments and modes of operation of the present invention have been described in the foregoing examples. The invention which is intended to be protected herein, however, is not to be construed limited to the particular forms disclosed, since these are to be regarded as illustrative rather than restrictive. Variations and changes may be made by those skilled in the art, without departing from the spirit of the invention.

General Procedure:

General procedures for preparation of compound IV, compound V and compound VI are given below.

A. Preparation of Compound IV (Scheme-3):

The reaction of substituted benzimidazothiol derivatives or substituted imidazopyridine-thiol derivatives (compound II) with substituted methoxypyridinium hydrochloride derivatives (compound III) was carried out at 25-30° C., in presence of aqueous solution of base such as sodium hydroxide and an organic solvent like methanol. The reaction was monitored by TLC and after completion of the reaction, the mixture was filtered, the solid was separated and dried to give the respective substituted methoxy-pyridinylmethylsulfidyl imidazole or imidazopyridine derivatives (compound IV).

B. Preparation of Compound V

B.1—(Using Sodium Sulfide):

The solution of compound IV in N-methyl pyrrolidone was treated with sodium sulfide at 80-110° C. The reaction was continued till completion of the reaction, as monitored by TLC. The reaction mass was cooled and pH was adjusted in the range of 6 to 7 using aqueous solution of acetic acid. Filtration of the obtained solid and drying gave compound V having desired purity.

B.2—(Using HBr/Acetic Acid):

A stirred mixture of compound IV, acetic acid and aqueous HBr was heated to 100-110° C. till the reaction was complete, as monitored by TLC. After completion, the reaction mass was cooled and concentrated under reduced pressure. The residue was diluted with water and washed with dichloromethane. The aqueous layer was neutralized by addition of sodium carbonate solution, which was followed by addition of methanol and filtered. The residue thus obtained was optionally washed with aqueous methanol and dried to give compound V.

B.3—(Using AlCl$_3$):

A mixture of compound IV, aluminium chloride were stirred in a solvent like chloroform and heated to 50-70° C. till the reaction was complete, as monitored by TLC. The reaction mass was cooled, quenched with water and concentrated. Hydrochloric acid was added to the residue and the aqueous layer was neutralized using aqueous sodium carbonate solution. The precipitated solid was filtered, dried, and optionally purified to give compound V.

C. Preparation of Compound VI

C.1: Oxidation with Camphorsulfonyl Oxaziridine:

(10-Camphorsulfonyl) oxaziridine was gradually added to a solution of compound V and sodium hydroxide in isopropyl alcohol at 25 to 30° C. and stirred at same temperature. After completion of the reaction, as monitored by TLC, the reaction mass was filtered, and the filtrate was concentrated under vacuum to obtain compound VI, which was directly used for further reaction. In some cases, the residue obtained after concentration was dissolved in methanol, concentrated and further treated with toluene and dried to obtain compound VI C.2: Oxidation with Sodium Hypochlorite:

Compound V was added to a stirred mixture of aqueous sodium hydroxide and methanol, followed by gradual addition of sodium hypochlorite solution at 25-30° C. The reaction mixture was stirred at the same temperature till completion of the reaction and then extracted with an organic solvent. The organic layer was concentrated to give the desired product. Alternatively, the reaction mass containing compound VI was carried forward for the next reaction, without isolating the product.

D—Preparation of Compound I:

A solution of compound VI dissolved in water or an organic solvent or mixtures thereof was treated with acid, which was gradually added to it at 25-30° C., till the pH of the reaction mixture was in the range of 4.5 to 8.5, preferably 6.5 to 8. The mass was stirred till completion of the reaction as monitored by TLC. The suspension thus obtained was filtered and solid was dried to get compound I, which was optionally purified using suitable methods.

EXAMPLES

Example 1

Preparation of 1-(5-(difluoromethoxy)-1H-benzo[d]imidazol-2-yl)-2-((2-(1-(5-(difluoromethoxy)-1H-benzo[d]imidazol-2-yl)-1,4-dihydro-3-methoxy-4-oxopyridin-2-yl)methyl)disulfinyl)methyl)-3-methoxypyridin-4(1H)-one [I-A-11]

Example 1A

Preparation of IV-A-11

Methanol (270 ml) was added to a solution of NaOH (41.5 gms) in water (180 ml), followed by addition of 5-difluoromethoxy-2-mercapto-1H-benzimidazole (105.2 gms). A solution of 2-chloromethyl-3,4-dimethoxy-pyridine.hydrochloride (100.3 gm in water (150 ml)) was gradually added to the reaction mixture and stirred at 25-30° C. till completion of the reaction. After completion, as monitored by TLC, the reaction mixture was filtered and the obtained solid was dried to give compound IV-A-11.

Yield: 140.6 gm (83%).

1H NMR (400 MHz, CDCl3): δ 8.27 (d, J=5.6 Hz, 1H), 7.48 (d, J=8.8 Hz, 1H), 7.32 (d, J=2 Hz, 1H), 6.99 (dd, J=2.4, 8.8 Hz, 1H), 6.87 (d, J=5.6 Hz, 1H), 6.50 (t, J=74.8 Hz, 1H), 4.39 (s, 2H), 3.95 (s, 3H), 3.93 (s, 3H).

ESI-MS: 368.9 (M+1).

Example 1B

Preparation of V-A-11

The solution of compound IV-A-11 (50.7 gms) and sodium sulfide (38.6 gm, assay 55%) in N-methyl pyrrolidone (700 ml) were heated to 90 to 100° C. and stirred at the same temperature. After completion of the reaction, as monitored by TLC, the reaction mass was quenched with water and pH was adjusted to 6.7 using aqueous acetic acid (50%). The obtained suspension was filtered and solid dried to get compound V-A-11.

Yield: 29.5 gm (61%).

$^1$H NMR (400 MHz, DMSO d$_6$): δ 7.66 (br. s, 1H), 7.48 (br. s, 1H), 7.30 (br. s, 1H), 7.16 (t, J=74.4 Hz, 1H), 6.98 (dd, J=2.0, 8.0 Hz, 1H), 6.25 (br. s, 1H), 4.54 (s, 2H), 3.76 (s, 3H), ESI-MS: 353.7 (M+1).

Example 1C

Preparation of 2-(5-difluoromethoxy-1H-benzoimidazole-2-sulfinylmethyl)-3-methoxy-pyridin-4-ol-disodium [VI-A-11]

(1R)-(−)-(10-camphorsulfonyl) oxaziridine (33.7 gm) was gradually added to a solution of V-A-11 (50.1 gm), and sodium hydroxide (12.4 gm) in isopropyl alcohol (350 ml) at 25 to 30° C. The reaction mixture was stirred at 25 to 30° C. The reaction mass was filtered and the filtrate was concentrated under vacuum to obtain VI-A-11 (60.1 gm) and carried forward for next reaction.

Example 1D

Preparation of [I-A-11]

Aqueous acetic acid (50%) was gradually added to a solution of VI-A-11 (190.5 gm) in ethyl acetate (1900 ml) and water (1140 ml) at 25 to 30° C. till the reaction mass attained pH 7.3. The mass was stirred till completion of the reaction as monitored by TLC. The suspension thus obtained was filtered and solid was dried to give compound I-A-11.

Yield: 14.1 gm (11%).

$^1$H NMR (400 MHz, DMSO d$_6$): δ 13.35 (br. s, 2H), 7.94 (d, J=7.6 Hz, 2H), 7.59 (br. s, 2H), 7.40 ((s, 6H br. s, 2H), 7.22 (t, J=74 Hz, 2H), 7.11 (d, J=8.4 Hz, 2H), 6.33 (d, J=7.6 Hz, 2H), 4.17 (s, 4H), 3.76 (s, 6H).

$^{13}$C NMR (100 MHz, DMSO d$_6$): δ 173.0, 147.9, 146.9, 146.3, 139.4, 137.5, 119.4, 116.8, 116.6, 115.7, 114.2, 59.6, 32.7.

ESI-MS: 705 (M+1).

Example 2

Preparation of 2-((2-((1-(1H-benzo[d]imidazol-2-yl)-1,4-dihydro-4-oxopyridin-2-yl)methyl)disulfinyl)methyl)-1-(1H-benzo[d]imidazol-2-yl)pyridin-4(1H)-one [I-A-1]

Example 2A

Preparation of 2-(−1H-benzoimidazole-2-sulfinylmethyl)-pyridin-4-ol-disodium [VI-A-1]

The experimental procedure that was followed was same as that described for synthesis of (VI-A-11) wherein compound (V-A-1, 72.8 g), sodium hydroxide (22.4 g), isopropyl alcohol (500 ml) and (1R)-(−)-(10-camphorsulfonyl) oxaziridine (67.9 g) were used to obtain compound (VI-A-1) which was used for further reactions.

Yield: 112.6 g

Example 2B

Preparation of [I-A-1]

The experimental procedure that was followed was same as that described for synthesis of (I-A-11) wherein compound (110.4 g), ethyl acetate (1100 ml), water (660 ml) and aqueous acetic acid (50%) were used to obtain (I-A-1).

Yield: 13.0 g $^1$H NMR (400 MHz, DMSO-d6): δ 13.25 (br. s, 2H, D$_2$O exchangable), 7.98 (d, J=8.0 Hz, 2H), 7.57 (s, 4H), 7.29-7.25 (m, 4H), 6.30 (d, J=2.4 Hz, 2H), 6.21 (dd, J=2.8, 8.0 Hz, 2H), 4.06 (s, 4H).

$^{13}$C NMR (100 MHz, DMSO): δ 177.7, 145.7, 145.3, 141.7, 122.9, 120.4, 116.7, 38.3. ESI-MS: 612.9 (M+1).

Example 3

Preparation of 2-((2-((1-(1H-benzo[d]imidazol-2-yl)-1,4-dihydro-3,5-dimethyl-4-oxopyridin-2-yl)methyl)disulfinyl)methyl)-1-(1H-benzo[d]imidazol-2-yl)-3,5-dimethylpyridin-4(1H)-one [I-A-2]

Example 3A

Preparation of 2-(1H-benzoimidazole-2-sulfinylmethyl)-3,5-dimethyl-pyridin-4-ol-disodium [VI-A-2]

(1R)-(−)-(10-camphorsulfonyl) oxaziridine (167.5 g) was gradually added to a mixture of (V-A-2) (200.7 g), and sodium hydroxide (57.2 g), in isopropyl alcohol (1400 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-2), which was used for further reactions. Yield: 235.6 g

Example 3B

Preparation of [I-A-2]

Aqueous acetic acid (50%) was gradually added to the stirred mixture of compound (VI-A-2), (130.4 g), in ethyl acetate (1300 ml) and water (780 ml) till the pH of the reaction mass was between 6.5 and 7.5. Reaction mass was stirred at room temperature till completion of the reaction as monitored by TLC. The reaction mass was filtered and the obtained solid was dried to give compound (I-A-2).

Yield: 21.5 g $^1$H NMR (400 MHz, CD3OD): δ 7.84 (s, 2H), 7.58-7.56 (m, 4H), 7.36-7.33 (m, 4H), 3.99 (s, 4H), 2.01 (s, 6H), 2.00 (s, 6H).

$^{13}$C NMR (100 MHz, DMSO $d_6$): δ 177.3, 146.0, 141.6, 137.5, 124.2, 122.9, 122.3, 115.5, 36.7, 13.3, 11.4.

ESI-MS: 569.1 (M+1).

Example 4

Preparation of 2-((2-((1-(1H-benzo[d]imidazol-2-yl)-1,4-dihydro-3-methoxy-4-oxopyridin-2-yl)methyl)disulfinyl)methyl)-1-(1H-benzo[d]imidazol-2-yl)-3-methoxypyridin-4(1H)-one [I-A-3]

Example 4A

Preparation of 2-(1H-benzoimidazole-2-sulfinylmethyl)-3-methoxy-pyridin-4-ol-disodium [VI-A-3]

(1R)-(−)-(10-camphorsulfonyl) oxaziridine (83.2 gms) was gradually added to a mixture of (V-A-3); (100.4 g) and sodium hydroxide (29.6 gms) in isopropyl alcohol (700 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-3), which was used for further reactions.

Yield: 137.8 g

Example 4B

Preparation of [I-A-3]

Aqueous acetic acid (50%) was gradually added to the stirred mixture of compound (VI-A-3); (120.3 g), in ethyl acetate (1200 ml) and water (720 ml), till the pH of the reaction mass was between 6.5 and 7.5. Reaction mass was stirred at room temperature till completion of the reaction as monitored by TLC. The reaction mass was filtered and the obtained solid was dried to give compound (I-A-3).

Yield: 26.6 g $^1$H NMR (400 MHz, DMSO $d_6$): δ 13.15 (br. s, 2H, $D_2O$ exchangable), 7.94 (d, J=7.6 Hz, 2H), 7.56 (br. s, 4H), 7.28-7.26 (m, 4H), 6.32 (d, J=7.6 Hz, 2H), 4.17 (s, 4H), 3.75 (s, 6H).

$^{13}$C NMR (100 MHz, DMSO $d_6$): δ 172.9, 147.9, 145.3, 139.5, 137.7, 122.9, 116.5, 59.6, 32.7.

ESI-MS: 573.1 (M+1).

Example 5

Preparation of 2-((2-((1,4-dihydro-3,5-dimethyl-1-(5-methyl-1H-benzo[d]imidazol-2-yl)-4-oxopyridin-2-yl)methyl)disulfinyl)methyl)-3,5-dimethyl-1-(5-methyl-1H-benzo[d]imidazol-2-yl)pyridin-4(1H)-one [I-A-4]

Example 5A

Preparation of 2-(5-methyl-1H-benzoimidazole-2-sulfinylmethyl)-3,5-dimethyl-pyridin-4-ol-disodium [VI-A-4]

The experimental procedure that was followed was same as that described for synthesis of (VI-A-3) wherein compound (V-A-4, (150.6 g), sodium hydroxide (41.9 g) isopropyl alcohol (1050 ml) and (1R)-(−)-(10-camphorsulfonyl) oxaziridine (119.3 g) were used to obtain compound (VI-A-4) which was used for further reactions.

Yield: 218.3 g.

Example 5B

Preparation of [I-A-4]

The experimental procedure that was followed was same as that described for synthesis of (I-A-3) wherein compound (VI-A-4), (200.3 g), ethyl acetate (2000 ml), water (1200 ml) and aqueous acetic acid (50%) were used to obtain (I-A-4).

Yield: 15.8 g $^1$H NMR (400 MHz, DMSO-d6): δ 13.05 (br. s, 2H, $D_2O$ exchangable), 7.89 (s, 2H), 7.6-7.2 (br. m, 4H), 7.09 (d, J=7.6 Hz, 2H), 4.10 (s, 4H), 2.42 (s, 6H), 1.90 (s, 6H), 1.88 (s, 6H)

$^{13}$C NMR (100 MHz, DMSO): δ 177.2, 145.4, 141.6, 137.4, 133.4, 133.0, 131.4, 124.1, 122.2, 118.8, 111.4, 36.7, 21.3, 13.3, 11.4.

ESI-MS: 597.0 (M+1).

Example 6

Preparation of 2-((2-((1,4-dihydro-3-methoxy-1-(5-methyl-1H-benzo[d]imidazol-2-yl)-4-oxopyridin-2-yl)methyl)disulfinyl)methyl)-3-methoxy-1-(5-methyl-1H-benzo[d]imidazol-2-yl)pyridin-4(1H)-one [I-A-5]

Example 6A

Preparation of 2-(5-methyl-1H-benzoimidazole-2-sulfinylmethyl)-3-methoxy-pyridin-4-ol-disodium [VI-A-5]

(1R)-(−)-(10-camphorsulfonyl) oxaziridine (87.2 gms) was gradually added to a mixture of (V-A-5) (110.5 gms), and sodium hydroxide (30.3 gms), in isopropyl alcohol (770 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-5), which was used for further reactions.

Yield: 155.4 g

Example 6B

Preparation of [I-A-5]

Aqueous acetic acid (50%) was gradually added to the stirred mixture of compound (VI-A-5), (150.8 g), in ethyl acetate (1200 ml) and water (720 ml), till the pH of the reaction mass was between 6.5 and 7.5. Reaction mass was stirred at room temperature till completion of the reaction as monitored by TLC. The reaction mass was filtered and the obtained solid was dried to give compound (I-A-5).

Yield: 24.0 g $^1$H NMR (400 MHz, DMSO $d_6$): δ 12.99 (br. s, 2H), 7.92 (d, J=7.6 Hz, 2H), 7.45 (d, J=7.6 Hz, 2H), 7.33 (s, 2H), 7.08 (d, J=8.0 Hz, 2H), 6.32 (d, J=7.6 Hz, 2H), 4.16 (s, 4H), 3.75 (s, 6H), 2.41 (s, 6H).

¹³C NMR (100 MHz, DMSO): δ 172.8, 147.8, 144.9, 139.4, 137.7, 132.3, 124.3, 116.5, 59.6, 32.8, 21.2.

ESI-MS: 600.9 (M+1).

Example 7

Preparation of 2-((2-((1,4-dihydro-1-(5-methoxy-1H-benzo[d]imidazol-2-yl)-3,5-dimethyl-4-oxopyridin-2-yl)methyl)disulfinyl)methyl)-1-(5-methoxy-1H-benzo[d]imidazol-2-yl)-3,5-dimethylpyridin-4(1H)-one [I-A-6]

Example 7A 2-(5-Methoxy-1H-benzoimidazole-2-sulfinylmethyl)-3,5-dimethyl-pyridin-4-ol-disodium [VI-A-6]

(1R)-(−)-(10-camphorsulfonyl) oxaziridine (74.4 g) was gradually added to a mixture of (V-A-6, 100.1 gms) and sodium hydroxide (25.4 g) in isopropyl alcohol (700 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-6) as pale yellow powder.

Yield: 60.6 g

¹H NMR (400 MHz, DMSO $d_6$): δ 7.54 (s, 1H), 7.32 (d, J=8.8 Hz, 1H), 6.98 (d, J=2.4 Hz 1H), 6.53 (dd, J=2.4, 8.8 Hz 1H), 4.23-4.12 (ABq, J=12.8 Hz, 2H), 3.71 (s, 3H), 1.96 (s, 3H), 1.84 (s, 3H).

¹³C NMR (100 MHz, DMSO $d_6$): δ 174.1, 161.9, 154.2, 146.9, 145.9, 141.4, 121.8, 121.3, 117.7, 109.7, 99.8, 61.9, 55.7, 15.2, 12.3.

ESI-MS: 331.8 (M+1).

Example 7B

Preparation of [I-A-6]

Aqueous acetic acid (50%) was gradually added to the stirred mixture of compound (VI-A-6; 15.3 gms) in ethyl acetate (150 ml) and water (90 ml) till the pH of the reaction mass was between 6.5 and 7.5. Reaction mass was stirred at room temperature till completion of the reaction as monitored by TLC. The reaction mass was filtered and the obtained solid was dried to give compound (I-A-6).

Yield: 4.5 g

¹H NMR (400 MHz, DMSO $d_6$): δ 13.0 (s, 2H, $D_2O$ exchangable), 7.88 (s, 2H), 7.47 (br. s, 2H), 7.03 (br. s, 2H), 6.88 (dd, J=2.0, 8.8 Hz, 2H), 4.09 (s, 4H), 3.79 (s, 6H), 1.90 (s, 6H), 1.88 (s, 6H).

¹³C NMR (100 MHz, DMSO $d_6$): δ 177.2, 156.3, 145.2, 141.7, 137.5, 124.0, 122.2, 112.6, 56.5, 36.8, 13.3, 11.4.

ESI-MS: 627 in negative ion mode.

Example 8

Preparation of 2-((2-((1,4-dihydro-3-methoxy-1-(5-methoxy-1H-benzo[d]imidazol-2-yl)-4-oxopyridin-2-yl)methyl)disulfinyl)methyl)-3-methoxy-1-(5-methoxy-1H-benzo[d]imidazol-2-yl)pyridin-4(1H)-one [I-A-7]

Example 8A

Preparation of 2-(5-methoxy-1H-benzoimidazole-2-sulfinylmethyl)-3-methoxy-pyridin-4-ol-disodium [VI-A-7]

(1R)-(−)-(10-camphorsulfonyl) oxaziridine (150.3 g) was gradually added to a mixture of (V-A-7) (200.2 g), and sodium hydroxide (52.1 g) in isopropyl alcohol (1400 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-7), which was used for further reaction.

Yield: 282.4 g

Example 8B

Preparation of [I-A-7]

Aqueous acetic acid (50%) was gradually added to the stirred mixture of compound (VI-A-7), (280.2 g) in ethyl acetate (2800 ml) and water (1680 ml) till the pH of the reaction mass was between 6.5 and 7.5. Reaction mass was stirred at room temperature till completion of the reaction as monitored by TLC. The reaction mass was filtered and the obtained solid was dried to give compound (I-A-7).

Yield: 63.8 g

¹H NMR (400 MHz, DMSO $d_6$): δ 12.99 (br. s, 2H, $D_2O$ exchangable), 7.91 (d, J=7.6 Hz, 2H), 7.51-6.87 (m, 6H), 6.32 (d, J=7.6 Hz, 2H), 4.13 (s, 4H), 3.79 (s, 6H), 3.76 (s, 6H).

ESI-MS: 633.0 (M+1).

Example 9

Preparation of 1-(5-fluoro-1H-benzo[d]imidazol-2-yl)-2-((2-((1-(5-fluoro-1H-benzo[d]imidazol-2-yl)-1,4-dihydro-3,5-dimethyl-4-oxopyridin-2-yl)methyl)disulfinyl)methyl)-3,5-dimethylpyridin-4(1H)-one [I-A-8]

Example 9A

Preparation of 2-(5-fluoro-1H-benzoimidazole-2-sulfinylmethyl)-3,5-dimethyl-pyridin-4-ol-disodium [VI-A-8]

(1R)-(−)-(10-camphorsulfonyl) oxaziridine (157.1 gms) was gradually added to a mixture of (V-A-8), (200.5 g) and sodium hydroxide (54.3 g) in isopropyl alcohol (1400 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-8), which was used for further reaction.

Yield: 300.1 g

Example 9B

Preparation of [I-A-8]

Aqueous acetic acid (50%) was gradually added to the stirred mixture of (VI-A-8) (200.2 g) in ethyl acetate (2000 ml) and water (1200 ml) till the pH of the reaction mass was between 6.5 and 7.5. Reaction mass was stirred at room temperature till completion of the reaction as monitored by TLC. The reaction mass was filtered and the obtained solid was dried to give compound (I-A-8).

Yield: 12.2 g $^1$H NMR (400 MHz, DMSO d$_6$): δ 13.36 (br. s, 2H, D$_2$O exchangable), 7.92 (s, 2H), 7.63-7.51 (br. m, 2H), 7.45-7.33 (br. m, 2H), 7.16-7.12 (m, 2H), 4.10 (s, 4H), 1.90 (s, 6H), 1.88 (s, 6H).

$^{13}$C NMR (100 MHz, DMSO d$_6$): δ 177.2, 160.0, 157.7, 146.9, 141.4, 137.3, 124.1, 122.3, 111.3, 36.7, 13.2, 11.4.

ESI-MS: 604.9 (M+1).

Example 10

Preparation of 1-(5-(trifluoromethyl)-1H-benzo[d]imidazol-2-yl)-2-((2-((1-(5-(trifluoromethyl)-1H-benzo[d]imidazol-2-yl)-1,4-dihydro-3-methoxy-4-oxopyridin-2-yl)methyl)disulfinyl methyl)-3-methoxypyridin-4(1H)-one [I-A-9]

Example 10A

Preparation of 2-(5-trifluoromethyl-1H-benzoimidazole-2-sulfinylmethyl)-3-methoxy-pyridin-4-ol-disodium [VI-A-9]

(1R)-(−)-(10-camphorsulfonyl) oxaziridine (52.5 g) was gradually added to a mixture of (V-A-9), (77.6 g) and sodium hydroxide (18.0 g) in isopropyl alcohol (540 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-9), which was used for further reaction.

Yield: 101.1 g

Example 10B

Preparation of [I-A-9]

Aqueous acetic acid (50%) was gradually added to the stirred mixture of (VI-A-9), (100.6 g) in ethyl acetate (1000 ml) and water (600 ml) till the pH of the reaction mass was between 6.5 and 7.5. Reaction mass was stirred at room temperature till completion of the reaction as monitored by TLC. The reaction mass was filtered and the obtained solid was dried to give compound (I-A-9).

Yield: 10.1 g $^1$H NMR (400 MHz, DMSO d$_6$): δ 7.98 (d, J=7.6 Hz, 2H), 7.92 (s, 2H), 7.75 (d, J=8.4 Hz, 2H), 7.58 (d, J=8.4 Hz, 2H), 6.35 (d, J=7.6 Hz, 2H), 4.20 (s, 4H), 3.77 (s, 6H).

$^{13}$C NMR (100 MHz, DMSO): δ 172.9, 147.9, 147.8, 139.3, 137.4, 124.8 (q, J=270 Hz, CF$_3$), 123.5 (q, J=31 Hz), 119.5, 116.6, 115.8, 113.6, 59.6, 32.8.

ESI-MS: 708.8 (M+1).

Example 11

Preparation of 1-(5-(difluoromethoxy)-1H-benzo[d]imidazol-2-yl)-2-((2-((1-(5-(difluoromethoxy)-1H-benzo[d]imidazol-2-yl)-1,4-dihydro-3,5-dimethyl-4-oxopyridin-2-yl)methyl)disulfinyl)methyl)-3,5-dimethylpyridin-4(1H)-one [I-A-10]

Example 11A

Preparation of 2-(5-difluoromethoxy-1H-benzoimidazole-2-sulfinylmethyl)-3,5-dimethyl-pyridin-4-ol-disodium [VI-A-10]

(1R)-(−)-(10-camphorsulfonyl) oxaziridine (123.4 gms) was gradually added to a mixture of (V-A-10), (182.3 gms), and sodium hydroxide (42.2 gms) in isopropyl alcohol (1270 ml) under stirring at room temperature. The reaction mixture was stirred at the same temperature till completion of the reaction as monitored by TLC and filtered. The filtrate was concentrated under reduced pressure to provide a residue, which was dissolved in methanol, concentrated and further treated with toluene and dried to obtain (VI-A-10), which was used for further reaction.

Yield: 220.1 g

Example 11B

Preparation of [I-A-10]

Aqueous acetic acid (50%) was gradually added to the stirred mixture of (VI-A-10) (220.1 g) in ethyl acetate (2200 ml) and water (1320 ml) till the pH of the reaction mass was between 6.5 and 7.5. Reaction mass was stirred at room temperature till completion of the reaction as monitored by TLC. The reaction mass was filtered and the obtained solid was dried to give compound (I-A-10).

Yield: 9.1 g $^1$H NMR (400 MHz, CD$_3$OD): δ 7.85 (s, 2H), 7.59 (d, J=8.8 Hz, 2H), 7.37 (s, 2H), 7.17 (d, J=8.8 Hz, 2H), 6.83 (t, J=74.4 Hz, 2H), 4.04 (s, 4H), 2.03 (s, 6H), 2.01 (s, 6H).

$^{13}$C NMR (100 MHz, CD$_3$OD): δ 180.5, 149.5, 147.8, 144.5, 139.2, 138.6, 126.6, 125.2, 120.7, 118.1, 118.0, 115.6, 107.6, 38.4, 13.7, 12.1.

ESI-MS: 701.0 (M+1).

Example 12

Preparation of 2-((2-((1,4-dihydro-1-(1H-imidazo[4,5-b]pyridin-2-yl)-3,5-dimethyl-4-oxopyridin-2-yl)methyl)disulfinyl)methyl)-1-(1H-imidazo[4,5-b]pyridin-2-yl)-3,5-dimethylpyridin-4(1H)-one [I-B-1]

Example 12A

Preparation of 2-(1H-imidazo-[6,7-c]pyridine-2-sulfinylmethyl)-3,5-dimethyl-pyridin-4-ol-disodium [VI-B-1]

The experimental procedure followed was same as that described for synthesis of (VI-A-11) wherein compound (V-B-I; (120.5 g), sodium hydroxide (34.6 g), isopropyl alcohol (840 ml) and (1R)-(−)-(10-camphorsulfonyl) oxaziridine (99.8 g) were used to obtain crude (VI-B-1) which was used for further reactions.

Yield: 200.3 g

Example 12B

Preparation of [I-B-1]

The experimental procedure followed was same as that described for synthesis of (I-A-11) wherein compound (VI-B-1); (200.6 g), ethyl acetate (2000 ml), water (1200 ml) and aqueous acetic acid (50%) were used to obtain (I-B-1).

Yield: 19.7 g $^1$H NMR (400 MHz, DMSO-d6): δ 8.25 (d, J=4.8 Hz, 2H), 8.03 (s, 2H), 7.92 (d, J=7.6 Hz, 2H), 7.14 (dd, J=4.8, 8.0 Hz, 2H), 4.32 (s, 4H), 1.90 (s, 6H), 1.86 (s, 6H)

$^{13}$C NMR (100 MHz, DMSO): δ 177.2, 153.2, 152.8, 142.0, 141.3, 137.6, 133.9, 124.2, 123.8, 121.9, 116.7, 37.4, 13.4, 11.5.

ESI-MS: 570.9 (M+1).

Example 13

Preparation of 2-((2-((1,4-dihydro-3-methoxy-1-(5-methoxy-1H-imidazo[4,5-b]pyridin-2-yl)-4-oxopyridin-2-yl)methyl)disulfinyl)methyl)-3-methoxy-1-(5-methoxy-1H-imidazo[4,5-b]pyridin-2-yl)pyridin-4(1H)-one [I-B-2]

Example 13A

Preparation of 2-(5-methoxy-1H-imidazo-[6,7-c]pyridine-2-sulfinylmethyl)-3-methoxy-pyridin-4-ol-disodium [VI-B-2]

The experimental procedure that was followed was same as that described for synthesis of (VI-B-1), wherein compound (V-B-2) (77.7 g), sodium hydroxide (19.1 g), isopropyl alcohol (540 ml) and (1R)-(−)-(10-camphorsulfonyl) oxaziridine (58.7 g) were used to obtain compound (VI-B-2) which was used for further reactions.

Yield: 147.2 gms.

Example 13B

Preparation of [I-B-2]

The experimental procedure that was followed was same as that described for synthesis of (I-B-1) wherein compound (VI-B-2), (140.3 g), ethyl acetate (1400 ml), water (840 ml) and aqueous acetic acid (50%) were used to obtain (I-B-2).

Yield: 25.6 g $^1$H NMR (400 MHz, DMSO-d6): δ 13.58 (br. s, 2H. D$_2$O exchangable), 7.93-7.90 (m, 4H), 6.74 (d, J=8.8 Hz, 2H), 6.31 (d, J=8.0 Hz, 2H), 4.16 (s, 4H), 3.88 (s, 6H), 3.77 (s, 6H).

$^{13}$C NMR (100 MHz, DMSO): δ 172.8, 161.1, 147.9, 144.3, 139.4, 137.5, 126.2, 116.5, 106.9, 59.6, 53.4, 32.7.

ESI-MS: 634.9 (M+1).

Example 14

Preparation of 2-((2-((1,4-dihydro-1-(5-methoxy-1H-imidazo[4,5-b]pyridin-2-yl)-3,5-dimethyl-4-oxopyridin-2-yl)methyl)disulfinyl)methyl)-1-(5-methoxy-1H-imidazo[4,5-b]pyridin-2-yl)-3,5-dimethylpyridin-4(1H)-one [I-B-3]

Example 14A

Preparation of 2-(5-Methoxy-3H-imidazo[6,7-c]pyridine-2-sulfinylmethyl)-3,5-dimethyl-pyridin-4-ol-disodium [VI-B-3]

(1R)-(−)-(10-camphorsulfonyl) oxaziridine (88.4 g) was gradually added to a mixture of (V-B-3; 80.2 gms) and sodium hydroxide (23.3 gms) in isopropyl alcohol (700 ml) under stirring at room temperature. The reaction mixture was stirred at the same temperature till completion of the reaction as monitored by TLC. When the reaction was complete, the solid was filtered off and the filtrate was concentrated under reduced pressure to obtain compound (VI-B-3) as a solid, which was used for further reaction.

Yield: 180.5 g

Example 14B

Preparation of [I-B-3]

Aqueous acetic acid (50%) was gradually added to the stirred mixture of compound (VI-B-3; 180.1 gms), dissolved in a mixture of ethyl acetate (1050 ml) and water (1500 ml) till the pH of reaction mass was 7.3. The reaction mass was stirred at room temperature till completion of the reaction as monitored by TLC. After completion, the reaction mass was filtered and the obtained solid was stirred in hydrochloric acid, filtered, washed with water and dried to give compound (I-B-3).

Yield: 63.8 g $^1$H NMR (400 MHz, DMSO d$_6$): δ 7.94-7.91 (m, 4H), 6.76 (d, J=8.8 Hz, 2H), 4.12 (s, 4H), 3.89 (s, 6H), 1.91 (s, 6H), 1.88 (s, 6H).

$^{13}$C NMR (100 MHz, DMSO d$_6$): δ 177.4, 161.4, 144.8, 142.0, 137.8, 124.5, 122.6, 107.2, 53.5, 37.0, 13.4, 11.5.

ESI-MS: 631.1 (M+1).

Spectral characterization of the aforementioned compounds was carried out as given below. The magnetic resonance spectra ($^1$H NMR and $^{13}$C NMR) were recorded on VARIAN 400-MR, while mass spectra were recorded on Applied Biosystems API2000 LC/MS/MS and SHIMADZU LC/MS 8030.

Example 15

Solid oral formulation (tablets) containing the active ingredient. A tablet containing compound (I) was prepared from the following ingredients:

| | Ingredients | % w/w |
|---|---|---|
| 1. | Active compound | 20 |
| 2. | Lactose | 73 |
| 3. | Methyl cellulose | 0.5 |
| 4. | Polyvinylpyrrolidone | 5.0 |
| 5. | Magnesium stearate | 1.5 |

The active ingredient was mixed with lactose, and granulated with a water solution of methyl cellulose. The wet mass was forced through a sieve and the granulate was dried in an oven. After drying, the granulate was mixed with polyvinylpyrrolidone and magnesium stearate. The dry mixture was pressed into tablet cores (10 000 tablets), each tablet containing 20% by weight of the active substance in a tableting machine using 6 mm diameter punches.

Details of evaluation of the activity of the aforementioned compounds are given below.

In Vitro Pharmacology

H+K+-ATPase assay Protocol Description:

Purpose

Evaluation of the effects of compounds on the activity of the $H^+/K^+$ATPase activity was quantified by measuring the formation of para-nitrophenol (p-NP) from para-nitrophenol phosphate (p-NPP) using an enzyme isolated from the rabbit or porcine (pig) fundus.

Experimental Protocol

The test compound, reference compound or water (control) are pre-incubated for 30 min at 37° C. with the enzyme (5 μg) in a buffer containing 40 mM Hepes/Tris (pH 6.0), 20 mM KCl, 5 mM $MgCl_2$ and 1 mM ouabain. The enzymatic reaction was then initiated by the addition of 2 mM p-NPP.

The absorbance was measured immediately at λ=405 nm using a microplate reader (EnVision, Perkin Elmer). This measurement at t=0 was also used to verify any compound interference with the spectrophotometric detection at the selected wavelength.

Thereafter, the mixture was incubated for 15 min at 37° C., after which time the reaction is stopped by addition of 0.5 M NaOH and a second measurement is made at the same wavelength (t=15). The enzyme activity is determined by subtracting the signal measured at t=0 from that measured at t=15. The results are expressed as a percent inhibition of the control enzyme activity.

The standard inhibitory reference compound is omeprazole,

Bibliographic reference: Dantzig, H., Minor, P. L. Garrigus, J. L., Fukuda, D. S. and Mynderse, J. S., Studies of the mechanism of action of A80915A, a semi-naphtolquinone natural product, as an inhibitor of gastric (H+/K+)-ATPase, Biochem. Pharmacol. (1991), 42: 2019.

General Information

Assay volume and format: 250 μl in 96-well plate

Compound addition: [100×] solution in solvent, then [10×] solution in water

Maximum tolerable DMSO concentration: 1%

TABLE C $IC_{50}$ values (rabbit, pig-porcine) of the compounds embodied in the present invention

| Serial No | Name of the compound | $IC_{50}$ (Rabbit) uM | $IC_{50}$ (Pig - Porcine) uM |
|---|---|---|---|
| 1 | I-A-1 | 1.0 | 1.8 |
| 2 | I-A-2 | 1.0 | 1.3 |
| 3 | I-A-3 | 1.1 | 2.0 |
| 4 | I-A-4 | 1.6 | 2.9 |
| 5 | I-A-5 | 1.3 | 2.3 |
| 6 | I-A-6 | 1.3 | 4.1 |
| 7 | I-A-7 | 1.2 | 4.7 |
| 8 | I-A-8 | 1.2 | 1.3 |
| 9 | I-A-9 | 1.1 | 1.7 |
| 10 | I-A-10 | — | — |
| 11 | I-A-11 | 1.5 | 3.3 |
| 19 | I-A-12 | — | — |
| 13 | I-A-13 | — | — |
| 14 | I-A-14 | — | — |
| 15 | I-B-1 | 2.8 | 14.0 |
| 16 | I-B-2 | 2.0 | 8.4 |
| 17 | I-B-3 | — | 45% @ 3-30 uM |
| 18 | Omeprazole | 4.0* | 3.9 ** |

*Literature reference: C. K Scott and E. Sundell, Inhibition of H + K + ATPase activity by SCH 28080 and SCH 32651, Eur. J Pharmacol, Jun. 7, (1985); 112(2): 268-70.
** Literature reference - D. J. Keeling, C Fallowfield, K. J. Milliner, S. K. Tingley, R. J. Ife, and A. H. Underwood, "Studies on the mechanism of action of omeprazole", Biochem Pharmacol, Aug. 15, (1985); 34(16): 2967-73.

In Vivo Pharmacology

The anti-ulcer efficacy of various test compounds (I-A-1 to I-A-11, I-B-1 to I-B-3) was assessed in Indomethacin—induced gastric ulceration model in female albino Wistar rats (Bhattacharya S., Banerjee D., Bauri A. K., Chattopadhyay S., Bandyopadhyay S. K. Healing property of the piper betelphenol, allylpyrocatechol against indomethacin-induced stomach ulceration and mechanism of action. World J Gastroenterol., 13(27): 3705-13, 2007; Lee A. Animal models of gastroduodenal ulcer disease. Bailliere's Best Pract. Res. Clinic Gastroenterol., 14(1): 75-96, 2000). The test compounds were administered orally at various doses (0.2, 0.4, 0.8 and 1.6 mg/kg) in comparison to Omeprazole (10 mg/kg) as standard comparator.

Experiments were conducted in overnight fasted healthy female albino Wistar rats maintained at controlled environmental conditions of temperature and humidity with water given ad libitum. Non-steroidal anti-inflammatory drug (NSAID), Indomethacin (30 mg/kg, p.o.) was used to induce gastric ulcer (treatment groups) with a comparative group without indomethacin treatment (negative group). Indomethacin was administered to treatment groups 1 hour after oral treatment with Vehicle (1% CMC), various doses of test compounds (EPPIs) and Omeprazole (10 mg/kg). After 4-6 hours after indomethacin administration, the animals were sacrificed by cervical dislocation and their stomach was dissected out. Various parameters like macroscopic ulcer index, gastric mucus content and gastric acid pH measurements were undertaken. The rat stomachs were cut opened along the greater curvature for macroscopic determination of ulcer index.

All the tested compounds at higher doses (1.6/0.8 mg/kg) produced very significant and equivalent anti-ulcerogenic effect in comparison to Omeprazole (10 mg/kg) in this Indomethacin—induced ulcer model in rats (Table D).

TABLE D

Anti-ulcer activity (indomethacin-induced ulcer model in rats) of the compounds embodied in the present invention

| Serial No. | Name of the compound | Indomethacin-induced ulcer model (dose @ which effect is similar to 10 mpk of omeprazole) mg/kg |
|---|---|---|
| 1 | I-A-1 | 1.6 |
| 2 | I-A-2 | 1.6 |
| 3 | I-A-3 | 1.6 |
| 4 | I-A-4 | 0.8/1.6 |
| 5 | I-A-5 | 1.6 |
| 6 | I-A-6 | — |
| 7 | I-A-7 | 1.6 |
| 8 | I-A-8 | 1.6 |
| 9 | I-A-9 | 1.6 |
| 10 | I-A-10 | 0.8/1.6 |
| 11 | I-A-11 | 1.6 |
| 12 | I-A-12 | — |
| 13 | I-A-13 | — |
| 14 | I-A-14 | — |
| 15 | I-B-1 | 1.6 |
| 16 | I-B-2 | 1.6 |
| 17 | I-B-3 | 1.6 |
| 18 | Omeprazole | 10 |

The invention claimed is:

1. Pyridone disulfide derivative of formula (I)

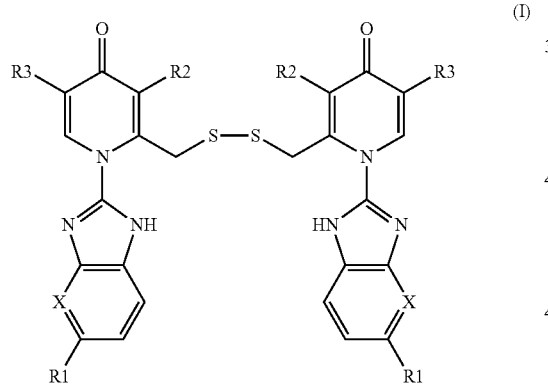

wherein, $R_1$, $R_2$ and $R_3$ are independently alkyl, alkoxy, halogen, halogenated alkoxy, halogenated alkyl, hydrogen and could be same or different, and X is CH.

2. Pyridone disulfide derivative of formula (I) according to claim 1, wherein $R_1$ is selected from the group consisting of methyl, methoxy, fluorine, trifluoromethyl, difluoromethoxy and hydrogen.

3. Pyridone disulfide derivative of formula (I) according to claim 1, wherein $R_2$ is selected from the group consisting of methyl, methoxy and hydrogen.

4. Pyridone disulfide derivative of formula (I) according to claim 1, wherein $R_3$ is selected from the group consisting of methyl and hydrogen.

5. The process for preparation of pyridone disulfide derivative of formula (I) according to claim 1 comprising treating compound (IV)

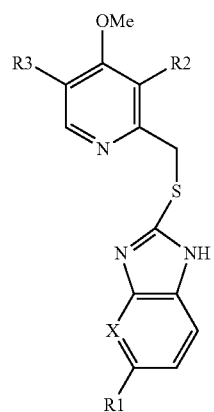

wherein $R_1$, $R_2$ and $R_3$ are as previously defined, with a dealkylating agent to give compound of formula (V),

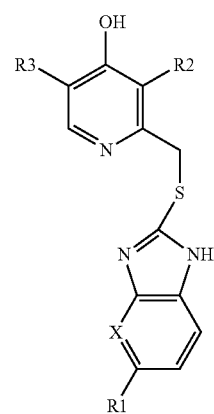

wherein $R_1$, $R_2$ and $R_3$ are as previously defined, oxidizing the compound of formula (V) with an oxidizing agent to give compound of formula (VI),

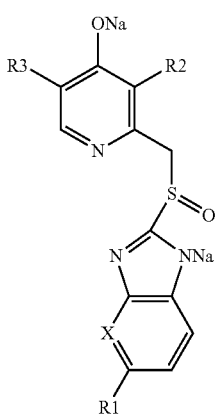

wherein $R_1$, $R_2$ and $R_3$ are as previously defined, and treating the compound of formula (VI) with an acid in presence of a solvent, in the pH range of 4.5 to 8.5, to give the pyridone disulfide derivative of formula (I).

6. The process according to claim 5, wherein the dealkylating agent is selected from the group consisting of sodium sulfide, hydrobromic acid and aluminium chloride.

7. The process according to claim 5, wherein the oxidizing agent is selected from 10-camphorsulfonyl oxaziridine and sodium hypochlorite.

8. The process according to claim 5 wherein the pyridone disulfide derivative of formula (I) is obtained by treating compound (VI) with an acid selected from the group consisting of an organic acid selected from the group consisting of acetic acid, citric acid, propionic acid, lactic acid, and mixtures thereof; a mineral acid selected from the group consisting of hydrochloric acid, sulfuric acid, nitric acid, and mixtures thereof; and a solvent selected from the group consisting of esters, alcohols, ketones, hydrocarbons, halogenated hydrocarbons, water and mixtures thereof.

9. A method for treatment of peptic ulcers, gastroesophageal reflux, or heartburns arising out of excessive secretion of acidic gastric fluids in a subject in need thereof, comprising administering to the subject a pharmaceutical composition of pyridone disulfide derivative of formula (I) according to claim 1.

10. Pyridone disulfide derivative of formula (I) according to claim 1 wherein the pyridone disulfide derivative is a compound selected from the group consisting of:

1-(5-(difluoromethoxy)-1H-benzo[d]imidazol-2-yl)-2-((2-((1-(5-(difluoromethoxy)-1H-benzo[d]imidazol-2-yl)-1,4-dihydro-3-methoxy-4-oxopyridin-2-yl)methyl)disulfinyl)methyl)-3-methoxypyridin-4(1H)-one (compound I-A-11);

2-((2-((1-(1H-benzo[d]imidazol-2-yl)-1,4-dihydro-4-oxopyridin-2-yl)methyl)disulfinyl)methyl)-1-(1H-benzo[d]imidazol-2-yl)pyridin-4(1H)-one (compound I-A-1);

2-((2-((1-(1H-benzo[d]imidazol-2-yl)-1,4-dihydro-3,5-dimethyl-4-oxopyridin-2-yl)methyl)disulfinyl)methyl)-1-(1H-benzo[d]imidazol-2-yl)-3,5-dimethylpyridin-4(1H)-one (compound I-A-2);

2-((2-((1-(1H-benzo[d]imidazol-2-yl)-1,4-dihydro-3-methoxy-4-oxopyridin-2-yl)methyl)disulfinyl)methyl)-1-(1H-benzo[d]imidazol-2-yl)-3-methoxypyridin-4(1H)-one (compound I-A-3);

2-((2((1,4-dihydro-3,5-dimethyl-1-(5-methyl-1H-benzo[d]imidazol-2-yl)-4-oxopyridin-2-yl)methyl)disulfinyl)methyl)-3,5-dimethyl-1-(5-methyl-1H-benzo[d]imidazol-2-yl)pyridin-4(1H)-one (compound I-A-4);

2-((2((1,4-dihydro-3-methoxy-1-(5-methyl-1H-benzo[d]imidazol-2-yl)-4-oxopyridin-2-yl)methyl)disulfinyl)methyl)-3-methoxy-1-(5-methyl-1H-benzo[d]imidazol-2-yl)pyridin-4(1H)-one (compound I-A-5);

2-((2-((1,4-dihydro-1-(5-methoxy-1H-benzo[d]imidazol-2-yl)-3,5-dimethyl-4-oxopyridin-2-yl)methyl)disulfinyl)methyl)-1-(5-methoxy-1H-benzo[d]imidazol-2-yl)-3,5-dimethylpyridin-4(1H)-one (compound I-A-6);

2-((2-((1,4-dihydro-3-methoxy-1-(5-methoxy-1H-benzo[d]imidazol-2-yl)-4-oxopyridin-2-yl)methyl)disulfinyl)methyl)-3-methoxy-1-(5-methoxy-1H-benzo[d]imidazol-2-yl)pyridin-4(1H)-one (compound I-A-7);

1-(5-fluoro-1H-benzo[d]imidazol-2-yl)-2-((2-((1-(5-fluoro-1H-benzo[d]imidazol-2-yl)-1,4-dihydro-3,5-dimethyl-4-oxopyridin-2-yl)methyl)disulfinyl)methyl)-3,5-dimethylpyridin-4(1H)-one (compound I-A-8);

1-(5-(trifluoromethyl)-1H-benzo[d]imidazol-2-yl)-2-((2-((1-(5-(trifluoromethyl)-1H-benzo[d]imidazol-2-yl)-1,4-dihydro-3-methoxy-4-oxopyridin-2-yl)methyl)disulfinyl methyl)-3-methoxypyridin-4(1H)-one (compound I-A-9);

1-(5-(difluoromethoxy)-1H-benzo[d]imidazol-2-yl)-2-((2-((1-(5-(difluoromethoxy)-1H-benzo[d]imidazol-2-yl)-1,4-dihydro-3,5-dimethyl-4-oxopyridin-2-yl)methyl)disulfinyl)methyl)-3,5-dimethylpyridin-4(1H)-one (compound I-A-10);

and pharmaceutically acceptable salts thereof.

11. A pharmaceutical formulation comprising a pyridone disulfide derivative of formula (I) according to claim 1 and a pharmaceutically acceptable carrier.

12. A pharmaceutical formulation comprising a pyridone disulfide derivative of claim 10 and a pharmaceutically acceptable carrier.

13. The pharmaceutical formulation of claim 11, wherein the pharmaceutical formulation is administered in the form of a tablet, coated tablet, granule, powder or capsule.

14. The pharmaceutical formulation of claim 12, wherein the pharmaceutical formulation is administered in the form of a tablet, coated tablet, granule, powder or capsule.

15. The pharmaceutical formulation of claim 11, wherein the pharmaceutical formulation is administered in the form of a subcutaneous, intramuscular or intravenous injection.

16. The pharmaceutical formulation of claim 12, wherein the pharmaceutical formulation is administered in the form of a subcutaneous, intramuscular or intravenous injection.

* * * * *